US012616809B2

(12) United States Patent
Reidt et al.

(10) Patent No.: US 12,616,809 B2
(45) Date of Patent: May 5, 2026

(54) METHOD FOR CARRYING OUT A P/V MANEUVER WHICH AUTOMATICALLY PREVENTS AN OVERDILATION OF THE LUNGS, AND VENTILATION DEVICE DESIGNED TO CARRY OUT THE METHOD

(71) Applicant: Hamilton Medical AG, Bonaduz (CH)

(72) Inventors: Sascha Reidt, Igis (CH); Christoph Schranz, Fläsch (CH); Dominik Novotni, Chur (CH)

(73) Assignee: Hamilton Medical AG, Bonaduz (CH)

( * ) Notice: Subject to any disclaimer, the term of this patent is extended or adjusted under 35 U.S.C. 154(b) by 1014 days.

(21) Appl. No.: 17/770,737

(22) PCT Filed: Oct. 28, 2020

(86) PCT No.: PCT/EP2020/080328
§ 371 (c)(1),
(2) Date: Apr. 21, 2022

(87) PCT Pub. No.: WO2021/083981
PCT Pub. Date: May 6, 2021

(65) Prior Publication Data
US 2022/0401670 A1 Dec. 22, 2022

(30) Foreign Application Priority Data
Oct. 31, 2019 (DE) ...................... 10 2019 129 549.1

(51) Int. Cl.
*A61M 16/00* (2006.01)
*A61B 5/091* (2006.01)
(52) U.S. Cl.
CPC ......... *A61M 16/0003* (2014.02); *A61B 5/091* (2013.01); *A61M 16/024* (2017.08);
(Continued)

(58) Field of Classification Search
CPC ............ A61M 16/0003; A61M 16/024; A61M 2016/0027; A61M 2016/003;
(Continued)

(56) References Cited

U.S. PATENT DOCUMENTS

| | | | | | |
|---|---|---|---|---|---|
| 5,303,700 | A | * | 4/1994 | Weismann | .......... A61M 16/024 |
| | | | | | 128/204.26 |
| 5,915,381 | A | | 6/1999 | Nord | |

(Continued)

FOREIGN PATENT DOCUMENTS

| | | |
|---|---|---|
| CN | 1764486 A | 4/2006 |

OTHER PUBLICATIONS

Japanese Office Action for corresponding JP 2022-523206 mailed Apr. 8, 2024, 3 pgs.
(Continued)

*Primary Examiner* — Brandy S Lee
*Assistant Examiner* — Tina Zhang
(74) *Attorney, Agent, or Firm* — Rankin, Hill & Clark LLP

(57) ABSTRACT

A ventilation device for artificially ventilating a patient, having a controller to actuate a flow modifying device for a P/V maneuver while wherein the pressure of respiratory gas is increased during an inspiration phase, wherein respiratory gas passively flows out of the patient during an expiration phase after the pressure increase is terminated, for a plurality of respiratory gas pressures, the respective maneuver respiratory gas volume in the patient from the P/V maneuver is ascertained in connection with the respiratory gas pressure during inspiration and expiration phases; the controller ascertaining a sequence of lung compliance values during the inspiration phase, ascertain a reference compliance value, based on the reference compliance value, determine a termination compliance value in the form of a threshold (Continued)

value as a termination criterion for the inspiration phase, and—terminate the inspiration phase if the termination compliance value is reached or exceeded.

19 Claims, 2 Drawing Sheets

(52) U.S. Cl.
CPC ............... *A61M 2016/0027* (2013.01); *A61M 2016/003* (2013.01); *A61M 2230/46* (2013.01)

(58) Field of Classification Search
CPC ...... A61M 2230/46; A61M 2205/3331; A61M 2205/3355; A61M 16/0051; A61M 2205/3334; A61M 2016/0036; A61B 5/091; A61B 5/085; A61B 5/087; G16H 20/40
See application file for complete search history.

(56) References Cited

U.S. PATENT DOCUMENTS

| | | | |
|---|---|---|---|
| 8,528,553 | B2 | 9/2013 | Wysocki et al. |
| 9,333,312 | B2 | 5/2016 | Cardelius et al. |
| 9,392,964 | B2 | 7/2016 | Mulqueeny et al. |
| 11,413,415 | B2 | 8/2022 | Isaza |
| 11,679,216 | B2 | 6/2023 | Hansmann et al. |
| 2003/0111078 | A1* | 6/2003 | Habashi ............ A61M 16/0003 128/204.18 |
| 2003/0225339 | A1* | 12/2003 | Orr ....................... A61B 5/0836 600/532 |
| 2012/0037159 | A1* | 2/2012 | Mulqueeny ....... A61M 16/0003 128/204.23 |
| 2012/0137249 | A1* | 5/2012 | Milne ............... A61M 16/0816 702/19 |
| 2013/0074844 | A1 | 3/2013 | Kimm et al. |
| 2014/0048072 | A1* | 2/2014 | Angelico ............ A61M 16/026 128/204.23 |
| 2019/0083726 | A1* | 3/2019 | Hansmann ............. A61B 5/087 |
| 2019/0134331 | A1 | 5/2019 | Meyer et al. |
| 2019/0275276 | A1 | 9/2019 | Kremeier |
| 2019/0388634 | A1 | 12/2019 | Enk et al. |

OTHER PUBLICATIONS

German Search Report for corresponding DE 10 2019 129 549.1 mailed Oct. 6, 2020, 10 pgs.
International Search Report for corresponding PCT/EP2020/080328 mailed Feb. 8, 2021, 17 pgs.
International Preliminary Report on Patentability for corresponding PCT/EP2020/080328 mailed May 3, 2022, 9 pgs.
Chinese Office Action for corresponding CN 202080076877.2 mailed Mar. 28, 2025, 6 pgs.

* cited by examiner

METHOD FOR CARRYING OUT A P/V MANEUVER WHICH AUTOMATICALLY PREVENTS AN OVERDILATION OF THE LUNGS, AND VENTILATION DEVICE DESIGNED TO CARRY OUT THE METHOD

This application claims priority in PCT application PCT/EP2020/080328 filed on Oct. 28, 2020, which claims priority in German Patent Application DE 10 2019 129 549.1 filed on Oct. 31, 2019, which are incorporated by reference herein.

The present invention concerns a ventilation device for artificial ventilation of a patient, comprising:

A respiratory gas source arrangement which provides an inspiratory respiratory gas for artificial ventilation of the patient, A flow modification device which is configured to produce and quantitatively modify an inspiratory respiratory gas flow, A respiratory gas line arrangement with a proximal longitudinal end which during operation lies nearer to the patient and with a distal longitudinal end which during operation lies further away from the patient, in order to convey the inspiratory respiratory gas flow from the respiratory gas source arrangement towards the patient, A flow sensor arrangement which is configured to acquire quantitatively both the inspiratory respiratory gas flow and an expiratory respiratory gas flow, A pressure sensor arrangement which is configured to acquire a pressure both of the inspiratory respiratory gas and of the expiratory respiratory gas in the respiratory gas line arrangement, A control device with a data memory, where the control device is connected for signal transmission with the data memory, with the flow sensor arrangement, and with the pressure sensor arrangement and which is configured to control the operational output of the flow modification device for modifying the inspiratory respiratory gas flow, Where the control device is configured to actuate the flow modification device for performing a P/V maneuver in which in an inspiration phase, respiratory gas is supplied to a patient under elevated respiratory gas pressure which in an expiration phase after completion of the pressure elevation flows passively out of the patient, where both during the inspiration phase and during the expiration phase, for a plurality of respiratory gas pressures, the particular maneuver respiratory gas volume present in the patient due to the P/V maneuver is determined and assigned to the prevailing respiratory gas pressure.

The present invention further concerns a method for performing a P/V maneuver on a patient's lung, preferably for the purpose of establishing data for assessing a recruitability and dilatability of pulmonary tissue of a patient's lung.

BACKGROUND OF THE INVENTION

A ventilation device of the type mentioned at the beginning and a method for performing a P/V maneuver on a patient's lung are known from EP 2 091 429 B1. This publication proposes to determine a positive end-expiratory pressure, hereunder referred to as 'PEEP' (for Positive End-Expiratory Pressure) in conformity with the professional world, for a particular patient by means of a P/V maneuver on the patient and/or the patient's lung, respectively.

In this P/V maneuver known from EP 2 091 429 B1, beginning with a start respiratory gas pressure under continuous elevation of the respiratory gas pressure, inspiratory respiratory gas is supplied to the patient until a predetermined inspiratory respiratory gas end-pressure is reached. An inspiratory P-V curve is recorded during this process, representing the inspiratory respiratory gas volume supplied to the patient during the inspiration phase of the P/V maneuver, always in correlation with the respective prevailing respiratory gas pressure.

Once the predetermined respiratory gas end-pressure is reached, as part of the still ongoing P/V maneuver the previously supplied respiratory gas is allowed to escape from the patient's lung as expiratory respiratory gas, once again under acquisition of the particular respiratory gas volume still present in the patient in correlation with the pressure of the expiratory respiratory gas prevailing during the respective acquisition. For this too, a P-V curve is recorded, this time as an expiratory P-V curve, representing the respiratory gas volume present in the patient during the expiration phase of the P/V maneuver in correlation with the expiratory respiratory gas pressure prevailing during the acquisition. The P/V maneuver ends at a predetermined end-pressure.

The inspiratory and the expiratory P-V curve traverse a common respiratory gas pressure range, where the two curves exhibit hysteresis. The expiratory P-V curve exhibits, over a wide mid-level respiratory gas pressure range, higher volumes at the same respiratory gas pressure values.

EP 2 091 429 B1 proposes to determine automatically, for the particular patient on whom the P/V maneuver is performed, a suitable PEEP as that pressure at which the expiratory and the inspiratory P-V curve exhibit the quantitatively greatest difference.

Since due to the characteristics of the two P-V curves, once a quantitatively greatest volume difference between the two P-V curves was acquired then under further decreasing pressure of the expiratory respiratory gas during the expiration phase, the volume difference between the expiratory and the inspiratory P-V curve decreases and no renewed increase of this volume difference is to be expected, EP 2 091 429 B1 recommends terminating the expiration phase of the P/V maneuver when during the expiration phase a quantitatively greatest volume difference could be detected between the expiratory and the inspiratory P-V curve.

A ventilation device is known from U.S. Pat. No. 5,915,381 which proposes calculating an instantaneous compliance of the ventilated patient's lung from an inspiratory P-V curve obtained during normal instrument-based ventilation of a patient, and modifying ventilation parameters, such as pressure levels, PEEP, inspiration period, expiration period, and respiratory rate when the instantaneous compliance of the lung is smaller than a predetermined threshold value.

"Compliance" indicates here, in the professional sense, elastic resistance of the lung to a change in volume. It is determined, in a known professional manner, from the ratio of a change in the lung's volume effected through a change in the pressure of respiratory gas. In contrast to a total compliance or mean compliance obtained over a complete inspiration phase, "instantaneous compliance" indicates compliance present at a concrete point in time and/or during a concrete inspiration state respectively.

U.S. Pat. No. 5,915,381 points out that depending on the pathological state of the particular ventilated lung, different respiratory gas quantities have to be supplied to the lung in order to prevent complete or part-collapse of the lung. A diseased lung usually has a smaller ventilation range than a healthy lung. Therefore, according to U.S. Pat. No. 5,915, 381, for each patient a specific compliance threshold value has to be predetermined with which the instantaneous compliance is compared during an instrument-based inspiration phase. U.S. Pat. No. 5,915,381 cites, as an additionally possible safety measure for some patients, terminating an inspiration phase as soon as the instantaneous compliance obtained during the inspiration phase falls below a predetermined threshold value.

In the present application, the term "compliance" refers to instantaneous compliance unless otherwise stated in a particular case.

At the beginning of an artificial inspiration of a lung, in its largely exhaled state, an increase in the inspiratory respiratory gas pressure leads initially to a relatively small pulmonary volume increase. The lung's compliance is, therefore, quantitatively low at the beginning of the inspiration phase of the P/V maneuver. After certain filling of the lung with inspiratory respiratory gas, the pulmonary volume increases more strongly with increasing pressure of the inspiratory respiratory gas than at the beginning of the P/V maneuver, such that in this temporally middle phase of the P/V maneuver the lung's compliance is quantitatively greater than at the beginning of the maneuver. Towards the end of the P/V maneuver, the already heavily with respiratory gas filled lung can no longer be enlarged volume-wise even under further increase in the pressure of the inspiratory respiratory gas, such that towards the end of a P/V maneuver the lung's compliance again decreases quantitatively.

U.S. Pat. No. 5,915,381 cites, therefore, the advantage of establishing for each patient a suitable compliance threshold value for influencing the pressure level, PEEP, inspiration period, expiration period, respiration rate, and the like, but places this establishing of a predetermined compliance threshold value ahead of the artificial ventilation during which the compliance threshold value is applied. Such patient-specific pre-calculation of a compliance threshold value in accordance with the patient's reported medical case history is costly and time-intensive. Furthermore, obtaining a patient-specific compliance threshold value and transmitting the same to the ventilation device is error-prone.

SUMMARY OF THE INVENTION

The task of the present invention is to develop the ventilation device known from EP 2 091 429 B1 in such a way that during the performing of a P/V maneuver, patients are well protected at the lowest possible cost against adverse health-related effects of the P/V maneuver and that measurement data obtained from the P/V maneuver are contaminated to the smallest possible extent by effects of a pulmonary overdilation.

The invention solves this task, in accordance with a device-based aspect, by means of a ventilation device of the type mentioned at the beginning, whose control device is configured To determine, during the inspiration phase of the P/V maneuver, on the basis of signals of the flow sensor arrangement and of the pressure sensor arrangement, a sequence of compliance values each of which represents a pulmonary compliance of the patient's lung, To determine, in accordance with the sequence of compliance values, a reference compliance value, To determine as a termination criterion for the inspiration phase, starting from the reference compliance value, a termination compliance value quantitatively different from the reference compliance value as a threshold value, and To terminate the inspiration phase when the termination compliance value is reached or crossed.

With the help of the flow sensor arrangement and the pressure sensor arrangement, the control device can straightforwardly determine a sequence of compliance values each of which represents a pulmonary compliance of the patient's lung at different points in time during the performing of the P/V maneuver. The flow sensor arrangement measures a flow, that is, volume flow, of inspiratory respiratory gas during the inspiration phase and of expiratory respiratory gas during the expiration phase. The flow or volume flow of respiratory gas corresponds to a change in the volume of respiratory gas in the patient's lung per unit of time.

The P/V maneuver can take place, for example, with a specified pressure increase rate of the respiratory gas pressure or with a specified inspiratory respiratory gas volume flow, for instance with a constant respiratory gas volume flow.

The flow sensor arrangement can exhibit several flow sensors, for instance one each for the inspiratory and for the expiratory respiratory gas flow. Preferably the flow sensor arrangement comprises only one flow sensor to acquire both the inspiratory and the expiratory respiratory gas flow. It is preferably arranged proximally between the respiratory gas line arrangement and the patient interface, but can also be accommodated distally in a housing of the ventilation device in which, for example, the flow modification device is also accommodated. To achieve higher process reliability, the ventilation device can also exhibit several flow sensors each of which acquires both the inspiratory and the expiratory respiratory gas flow, for instance a distal flow sensor in a housing of the ventilation device and a proximal flow sensor near the patient. The same applies mutatis mutandis to the pressure sensor arrangement, which likewise can exhibit or several pressure sensors in order to measure both the pressure of the inspiratory and of the expiratory respiratory gas.

By integrating the respiratory gas flow over a period of time, the volume of respiratory gas which during that time has flowed into the respiratory gas line arrangement can be determined. This is also the volume of respiratory gas which during that time has either been supplied to the lung as inspiratory respiratory gas or flowed out of the lung as expiratory respiratory gas.

To distinguish it from arbitrary other respiratory gas volumes which can occur during artificial ventilation or during a P/V maneuver, in the present application the respiratory gas volume present in the patient's lung during a P/V maneuver through the supply of inspiratory respiratory gas to the patient's lung and through the flow of expiratory respiratory gas out of the patient's lung is referred to as "maneuver respiratory gas volume". In the event o doubt, the maneuver respiratory gas volume during the inspiration phase is the integral of the inspiratory respiratory gas flow over time during the inspiration phase, and the maneuver respiratory gas volume during the expiration phase is the value of the integral of the inspiratory respiratory gas flow at the end of the inspiration phase less the integral of the expiratory respiratory gas flow over time during the expiration phase. The maneuver respiratory gas volume can consequently be depicted as a function of time from the beginning of the inspiration phase until the end of the expiration phase. Since the respiratory gas pressure in the respiratory gas line arrangement can also be depicted as a function of time, the maneuver respiratory gas volume can also be depicted as a function of the respiratory gas pressure in the respiratory gas line arrangement during the inspiration phase and during the expiration phase.

In the present application, the functional relationship between the particular maneuver respiratory gas volume present and the respiratory gas pressure prevailing meanwhile is referred to as a P-V curve or P-V relationship.

Preferably the ventilation device also comprises a time-measuring device in order to be able to determine time durations of processes and part-processes during the P/V maneuver and points in time during the P/V maneuver. With the help of the time-measuring device, a change in the respiratory gas pressure, be it the pressure of an inspiratory or an expiratory respiratory gas, can also be accurately determined. However, a time-measuring device is not obligatory. For example, the control device can be configured to interrogate sensor signals at predetermined known time intervals, such that a known time duration always elapses between the individual interrogated acquired values of the sensor arrangements. A temporal change in relevant parameters, such as for instance respiratory gas pressure or respiratory gas volume, can also be determined in this way sufficiently accurately.

The compliance values thus determined are directly a patient-specific property of the lung of the particular ventilated patient. Therefore, without great cost, a reference compliance value can be adduced from the sequence of compliance values which likewise is specific for the particular ventilated patient.

If, starting from the reference compliance value thus determined, a termination compliance value is then determined on reaching or crossing which the inspiration phase is terminated, it is possible to prevent the patient being subjected to "over-inspiration" during the P/V maneuver, i.e. the patient's lung being overdilated or generally stressed or even damaged by an excessive quantity of respiratory gas and/or by an excessive respiratory gas pressure. Furthermore, due to the volume of the thoracic cavity accommodating the lung being limited by the ribcage, overdilation of the lung often results in adverse stressing of the cardiovascular system of the ventilated patient. This is because the overdilated lung takes up space at the expense of compressible tissues, such as for instance blood vessels and the like.

Consequently the control device can, from the data obtained through sensors during the inspiration phase of the P/V maneuver, automatically determine and use for each patient a suitable individual termination compliance value as threshold value for terminating the inspiration phase. Costly recording of the patient's medical case history in order to determine a predetermined termination compliance value and a potential error in transmitting it to the ventilation device can, therefore, be avoided.

The control device can, therefore, be configured to already terminate the inspiration phase of each P/V maneuver in a patient-protecting manner based on the termination criterion determined during the particular P/V maneuver itself. Consequently, the control device can be further configured to utilize during the uninterrupted artificial ventilation of one and the same patient quantitatively different termination compliance values as threshold value and termination criterion, depending on the particular state of health of the patient's lung. The control device can in particular be configured during an uninterrupted artificial ventilation of one and the same patient to determine a termination compliance value during each breath or during each second breath or during each nth breath, where n is a whole number, and to utilize it for the breath in which it is determined, preferably until a subsequent termination compliance value is determined.

In principle there exist different options how the control device can determine the sequence of compliance values online, i.e. during a running P/V maneuver, from the aforementioned sensor signals. For example, the control device can be configured to calculate the sequence of compliance values on the basis of a ratio of a volume change value associated with respiratory gas pressure and a pressure change value associated with the same respiratory gas pressure, where the volume change value represents a temporal change in the maneuver respiratory gas volume and where the pressure change value represents a temporal change in the respiratory gas pressure. Thus, to this end there suffice the acquisition of two volume values at different points in time, from which the volume change value can be determined, and the acquisition of two respiratory gas pressure values at different points in time, preferably at the same points in time at which the two volume values are acquired, such that therefrom a pressure change value can be determined. This is a method based on differential ratios.

Alternatively, or additionally in order to provide redundancy, the control device can be configured to calculate the sequence of compliance values based on a ratio of a flow value associated with a respiratory gas pressure and the pressure change value associated with the same respiratory gas pressure, where the flow value represents the inspiratory respiratory gas flow. As already described above, the flow value is a measure of the change in the respiratory gas volume supplied to the lung or escaping from the lung per unit of time. This too, is a determination method based on differential ratios.

Attention should be paid here to ensure that the volume change value and the pressure change value apply for a matching time interval, preferably for a matching point in time, such that the volume change value and the pressure change value correspond temporally with one another. If the respiratory gas pressure changes with time and if the respiratory gas volume present in the patient's lung changes with time, then because of the change in the respiratory gas pressure, the waste gas volume present in the patient's lung changes with the respiratory gas pressure. The same applies mutatis mutandis to the flow value and to the pressure change value.

A certain temporal imprecision in the matching between the acquisition points in time of the respective necessary sensor values is acceptable. However, the better the matching of the acquisition points in time of the necessary sensor values, the more accurate the compliance calculated from them.

Different options also exist for determining the reference compliance value.

According to a first preferred embodiment, the control device can be configured to select, from a sequence of compliance values which from the start of the inspiration phase of the P/V maneuver become quantitatively first larger and subsequently smaller, the quantitatively largest compliance value as reference compliance value. The selected reference compliance value is advantageously stored temporarily in the data memory of the control device.

If one regards the distinct relationship, observed during a P/V maneuver, between the respiratory gas volume present in the patient's lung and the respiratory gas pressure prevailing in each case in the respiratory gas line arrangement, then the compliance is the first derivative with respect to the respiratory gas pressure of the respiratory gas volume which is changing with the respiratory gas pressure. It can be determined through differential ratios by using discrete measurement points in a way that is known per se, or through interpolation of discrete measurement points through a differentiable function and through a derivative of same, to name just two methods.

Put more simply: The compliance is the slope of the graph of the inspiratory maneuver respiratory gas volume as a function of the respiratory gas pressure. Due to the change in the compliance during the inspiration phase of a P/V maneuver as shown at the beginning, the graph of the maneuver respiratory gas volume as a function of the respiratory gas pressure exhibits a section with concave curvature lying nearer to the start respiratory gas pressure of the P/V maneuver and a section with convex curvature lying nearer to the end-pressure of the P/V maneuver. Usually, the inflection point at the transition between these two sections with different directions of curvature exhibits a quantitatively very large or even the quantitatively greatest compliance of the inspiratory P-V curve. The start respiratory gas pressure and the end-pressure of the P-V maneuver can be quantitatively equal pressures. They can also, however, be different, where preferably the end-pressure is then a lower absolute pressure of the respiratory gas than the start respiratory gas pressure. In principle, the start respiratory gas pressure can be chosen freely within the limits of what makes sense medically. Preferably, a pressure is chosen as the start respiratory gas pressure which lies in a pressure range extending from the PEEP determined for the particular patient up to approximately 1.6 times the PEEP, inclusive of the limits of the range.

Therefore, additionally or alternatively, the control device can be configured to determine, from a sequence of value-pairs of a respiratory gas pressure and the inspiratory maneuver respiratory gas volume associated with the respective respiratory gas pressure, an inflection point between sections curved in different directions of curvature of a graph representing the sequence of value-pairs, and to select the compliance value associated with the respiratory gas pressure at the inflection point as reference compliance value. In order to determine the inflection point, the control device can be configured, in a way which is known per se, to form the second derivative of the volume values as a function of the pressure values with respect to the pressure. According to an alternative this can take place, like the determination of the first derivative, through interpolation of obtained measurement values with a twice differentiable function and through differentiation of same. The reference compliance then lies at the respiratory gas pressure value at which the second derivative sequence of value-pairs exhibits the value zero or a value lying quantitatively nearest to zero. According to a further alternative, forming the second derivative can, just like determining the first derivative, take place through differential ratios.

Preferably, the sequence of the aforementioned value-pairs forms a P-V curve.

Through the two aforementioned preferred ways of choosing and/or determining respectively a reference compliance value, for a start a reference compliance value is chosen which from experience lies in a temporally middle range of the inspiration phase of the P/V maneuver at which with a probability bordering on certainty there is no over-stressing of the lung by the artificial inspiration. Besides, starting from the reference compliance value thus chosen, the compliance values occurring during the further inspiration phase are quantitatively smaller than the reference compliance value, such that starting from the reference compliance value, a meaningful termination compliance value can be obtained with a high degree of reliability.

In order to determine the termination compliance value, the control device can be configured to calculate the termination compliance value through multiplying the reference compliance value by a predetermined factor or through adding the reference compliance value to a predetermined summand. Preferably the predetermined summand is negative, since due to the nature of the course of the compliance value during the inspiration phase as described above, usually the termination compliance value is quantitatively smaller than the maximum compliance value preferred as a reference compliance value. For the same reason, preferably the predetermined factor is smaller than 1.

In a preferred embodiment example, the termination compliance value can equal 75% to 95%, preferably 80% to 92.5%, especially preferably 85% to 91% of the reference compliance value. Especially preferably, the termination compliance value equals approximately 90% of the reference compliance value if the latter is chosen in the vicinity of the maximum occurring compliance value, i.e. approximately in a range of 40% to 60% of the maximum occurring compliance value. This applies regardless of the method of calculating the termination compliance value starting from the reference compliance value. In this way overstressing, in particular overdilation, of the patient's lung during the inspiration phase can be reliably avoided.

In principle it is conceivable to perform the P/V maneuver, as known from the state of the art, for determining a PEEP which is especially suitable for the particular ventilated patient.

It has been shown, however, that a robust and reliable statement about the expected success of a recruitment procedure for recruiting a functional lung volume can be obtained through the P/V maneuver.

The use of the aforementioned termination criterion of the termination compliance value is of particular advantage here, because thereby it is possible to avoid using, in assessing the expected success of a recruitment procedure, values acquired during pulmonary overstressing which therefore would adversely falsify the assessment result if included in the assessment.

Notwithstanding and alternatively to the previously described method for avoiding the acquisition of values during pulmonary overstressing, in particular pulmonary overdilation, by the automated determination of a termination compliance value, the undesirable acquisition of values during pulmonary overdilation can also be effected as follows according to less preferred embodiments:

According to a first alternative, a predetermined negative value of the second derivative of the P/V curve can serve as termination criterion. The second derivative can be determined by the control device as described above. As at least one further additional criterion, the termination criterion can be activated by the control device only after a zero crossing of the second derivative or after previously acquired positive values of the second derivative.

According to a second alternative, a first P/V maneuver without determining an inspiratory termination criterion can initially be performed, as known from the state of the art. If pulmonary overdilation is ascertained during this first P/V maneuver, the control device can be configured to perform a second P/V maneuver with reduced end-pressure. If no pulmonary overdilation is ascertained during the first P/V maneuver, the values obtained during the first P/V maneuver and/or the obtained P-V curve are used for assessing the recruitability of the lung, otherwise the values obtained during the second P/V maneuver and/or the obtained P-V curve are used.

According to a third alterative, the control device is configured to decrease by a predetermined amount an end-pressure obtained by an operator or from a retrievable data source for a P/V maneuver, either through subtracting a predetermined safety margin or through multiplying by a value smaller than 1, preferably by a value between 0.78 and 0.92, for instance 0.8.

The control device can be configured to carry out one of the three aforementioned alternatives.

Reliable assessment of the prospects of success of a recruitment procedure directly from data of a P/V maneuver is so advantageous because it can replace performing a computerized tomography examination. Consequently, in the event of an at least partly collapsed lung, the ventilated patient can be examined directly in the hospital bed with regard to the prospects of success of a recruitment procedure. The recruitment procedure can be any recruitment procedure known in the medical community.

In order to provide the data needed for assessing the success prospects of a recruitment procedure of the particular ventilated patient, the control device can be configured to calculate a volume ratio value from > The quantitatively largest difference occurring during the P/V maneuver for a respiratory gas pressure between the expiratory and the inspiratory maneuver respiratory gas volume, and > A differential value between a maneuver respiratory gas volume value in an upper end-region and a maneuver respiratory gas volume value in a lower end-region of the respiratory gas pressure range traversed during the P/V maneuver, Where the lower end-region contains a start respiratory gas pressure at which the P/V maneuver begins and extends up to 1.05 times the start respiratory gas pressure, and where the upper end-region contains a termination respiratory gas pressure with which the termination compliance value is associated and begins at 95% of the termination respiratory gas pressure.

For a final assessment of the prospects of success of a later recruitment procedure, the control device can but does not have to be configured to generate, when the volume ratio value exceeds a predetermined first threshold value, an output which indicates that a recruitment procedure for recruiting the patient's lung has overwhelming prospects of success. This predetermined first threshold value preferably lies between 38% and 46%, where in investigations thus far 42% has proved to be the most suitable first threshold value, in order to distinguish a prospectively successfully recruit-able patient's lung from a prospectively not successfully recruitable patient's lung.

Alternatively or additionally, the control device can be configured, in order to provide the data needed for assessing the success prospects of a recruitment procedure of the particular ventilated patient, to calculate a hysteresis ratio value from > The size of the hysteresis area which the graphs of the expiratory and of the inspiratory maneuver respiratory gas volumes as functions of the respiratory gas pressure between a start respiratory gas pressure at which the P/V maneuver begins and a termination respiratory gas pressure associated with the termination compliance value, and > The area of a rectangle enclosing the hysteresis area whose one corner is determined by a lower respiratory gas pressure value in a lower end-region of the respiratory gas pressure range traversed during the P/V maneuver and by the respiratory gas volume value associated with the lower respiratory gas pressure value, Where the lower end-region contains the start respiratory gas pressure and extends up to 1.05 times the start respiratory gas pressure and whose diagonally opposite corner is determined by an upper respiratory gas pressure value in an upper end-region and by the respiratory gas volume value associated with the upper respiratory gas pressure value, where the upper end-region contains a termination respiratory gas pressure associated with the termination compliance value and begins at 95% of the termination respiratory gas pressure.

In order to assess from the aforementioned data the prospects of success of a recruitment procedure, the control device can but does not have to be configured to generate, when the hysteresis ratio value exceeds a predetermined second threshold value, an output which indicates that a recruitment procedure for recruiting the patient's lung has overwhelming prospects of success. Preferably the second threshold value is quantitatively different from the first threshold value. For the hysteresis ratio value, a second threshold value in a range from 28% to 36% has proved to be diagnostically meaningful. Based on investigations thus far, preferably the second threshold value lies near 32%.

It should be added that the respiratory gas source arrangement of the ventilation device can exhibit, as a respiratory gas source, an aspiration port through which ambient air or gas can be aspirated from a predetermined gas reservoir. The respiratory gas source arrangement can additionally or alternatively exhibit a gas reservoir as respiratory gas-source, for example as a storage tank or as a connector formation for connecting a supply line which links the ventilation device with a locally installed gas reservoir, as is often the case in hospitals. In order to provide the option of mixing different gases to form a respiratory gas, the respiratory gas source arrangement can exhibit a plurality of individual respiratory gas sources, such as the ones mentioned above. Due to their preparation and decompression, the different gases can exhibit different temperatures and/or different humidities. In order to be certain that the inspiratory respiratory gas actually reaches the patient at the humidity set for it, especially preferably no respiratory gas component is added any more in the inspiration direction downstream from a preferably present humidification device to the respiratory gas flow emerging from the humidification device.

The task mentioned at the beginning is also solved through a method for performing a P/V maneuver on a patient's lung, in particular for establishing data for assessing the recruitability of pulmonary tissue, the method comprising the following steps:

> Performing a P/V maneuver while supplying inspiratory respiratory gas to a patient in an inspiration phase under elevation of the respiratory gas pressure, > During the inspiration phase: Determining an inspiratory maneuver respiratory gas volume supplied during the inspiration phase or an inspiratory maneuver volume flow of inspiratory respiratory gas and determining the respiratory gas pressure, > Determining a sequence of compliance values each of which represents a pulmonary compliance of the patient's lung, > Determining a reference compliance value from the sequence of compliance values in accordance with the sequence of compliance values, Determining, starting from the reference compliance value, a termination compliance value quantitatively different from the reference compliance value as a termination threshold value, and Terminating the inspiration phase when the termination compliance value is reached or crossed.

Preferably the present invention also concerns a device configured for performing the aforementioned method. Preferably this is the previously described and developed ventilation device.

Method aspects set out during the description of the ventilation device are developments of the method according to the invention and device aspects set out during the description of the method according to the invention are developments of the ventilation device according to the invention.

As already described above, overstressing of the patient's lung by excessively high respiratory gas pressure can be prevented by means of the method. Along with the prevention of overstressing, in particular pulmonary overdilation, the acquisition of measurement values or measurement value-pairs in an overstressed state of the lung is also avoided. Compared with value-pairs acquired in a normally stressed state of the lung, results of measurement value-pairs acquired in an overstressed state have only a limited diagnostic power or even falsify a measurement outcome to which they belong.

In order to be able to obtain from the P/V maneuver data for the further treatment of a ventilated patient, preferably the inspiration phase is followed temporally by an expiration phase in which respiratory gas flows passively out of the patient, where during the expiration phase both the expiratory respiratory gas pressure and an expiratory maneuver respiratory gas volume value are determined, where the expiratory maneuver respiratory gas volume value represents an expiratory maneuver respiratory gas volume present in the patient during the expiration phase due to the P/V maneuver.

Both in the method according to the invention and in the device, in particular ventilation device, according to the invention, during the P/V maneuver maneuver respiratory gas volume values are acquired and stored as value-pairs and/or as value relationships in association with a respiratory gas pressure. A maneuver respiratory gas volume value is associated with the respiratory gas pressure present during its acquisition.

Whereas it is relatively simple to determine the inspiratory maneuver respiratory gas volume value, for example by integrating the flow values since the beginning of the inspiration phase, determining the expiratory maneuver respiratory gas volume value requires a higher computational cost. Determining the expiratory maneuver respiratory gas volume value within the scope of the method according to the invention can comprise, for example:

Determining a volume of expiratory respiratory gas exhaled during the expiration phase, and/or Determining an expiratory maneuver volume flow of expiratory respiratory gas.

The expiratory maneuver respiratory gas volume value can then be determined from the inspiratory maneuver respiratory gas volume value at the end of the inspiration phase less either the determined exhaled volume or the maneuver volume flow integrated over the duration thus far of the expiration phase.

The method for establishing data for later assessment of the success prospects of a recruitment procedure in the particular patient's lung can furthermore comprise: Calculating a volume ratio value from the quantitatively greatest difference, occurring during the P/V maneuver for a respiratory gas pressure, between the expiratory and the inspiratory maneuver respiratory gas volume, and a reference maneuver respiratory gas volume in an upper end-region of the respiratory gas pressure range traversed during the P/V maneuver, where the upper end-region contains a termination respiratory gas pressure associated with the termination compliance value and begins at 95% of the termination respiratory gas pressure. The above discussion regarding the volume ratio value in connection with the ventilation device according to the invention, applies here in particular.

Alternatively or additionally, the method for establishing data for later assessment of the success prospects of a recruitment procedure in the particular patient's lung can comprise: Calculating a hysteresis ratio value from The size of the hysteresis area which the graphs of the expiratory and the inspiratory maneuver respiratory gas volumes as functions of the respiratory gas pressure between the start respiratory gas pressure at which the P/V maneuver begins and a termination respiratory gas pressure associated with the termination compliance value, and The area of a rectangle enclosing the hysteresis area whose one corner is determined by a lower respiratory gas pressure value in a lower end-region of the respiratory gas pressure range traversed during the P/V maneuver and by the respiratory gas volume value associated with the lower respiratory gas pressure value, Where the lower end-region contains the start respiratory gas pressure and extends up to 1.05 times the start respiratory gas pressure and whose diagonally opposite corner is determined by an upper respiratory gas pressure value in an upper end-region and by the respiratory gas volume value associated with the upper respiratory gas pressure value, where the upper end-region contains a termination respiratory gas pressure associated with the termination compliance value and begins at 95% of the termination respiratory gas pressure.

As described above in connection with the ventilation device, after establishing the data the method can further exhibit a data evaluation step for assessing the success prospects of a recruitment procedure. To this end, the method can exhibit a step of comparing the volume ratio value with a predetermined first threshold value, where depending on the comparison result an output is generated which indicates whether a recruitment procedure for recruiting the patient's lung has overwhelming prospects of success or not. The discussion above applies to the predetermined first threshold value.

Preferably when the volume ratio value exhibits an amount exceeding the first threshold value, an output is generated which indicates that the recruitment procedure has overwhelming prospects of success. Preferably, otherwise no indication is output or an indication with an opposite content is output.

In order to assess the prospects of a successful recruitment procedure from the aforementioned hysteresis ratio value, the method can exhibit the step of comparing the hysteresis ratio value with a predetermined second threshold value, where depending on the comparison result an output is generated which indicates whether a recruitment procedure for recruiting the patient's lung has overwhelming prospects of success or not. The discussion above applies in turn to the second threshold value. Based on investigations thus far, preferably the second threshold value lies near 32%. Preferably when the hysteresis ratio value exceeds the predetermined second threshold value, an output is generated which indicates that a recruitment procedure for recruiting the patient's lung has overwhelming prospects of success.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which forms a part hereof and wherein.

DESCRIPTION OF PREFERRED EMBODIMENTS

Figure 1:
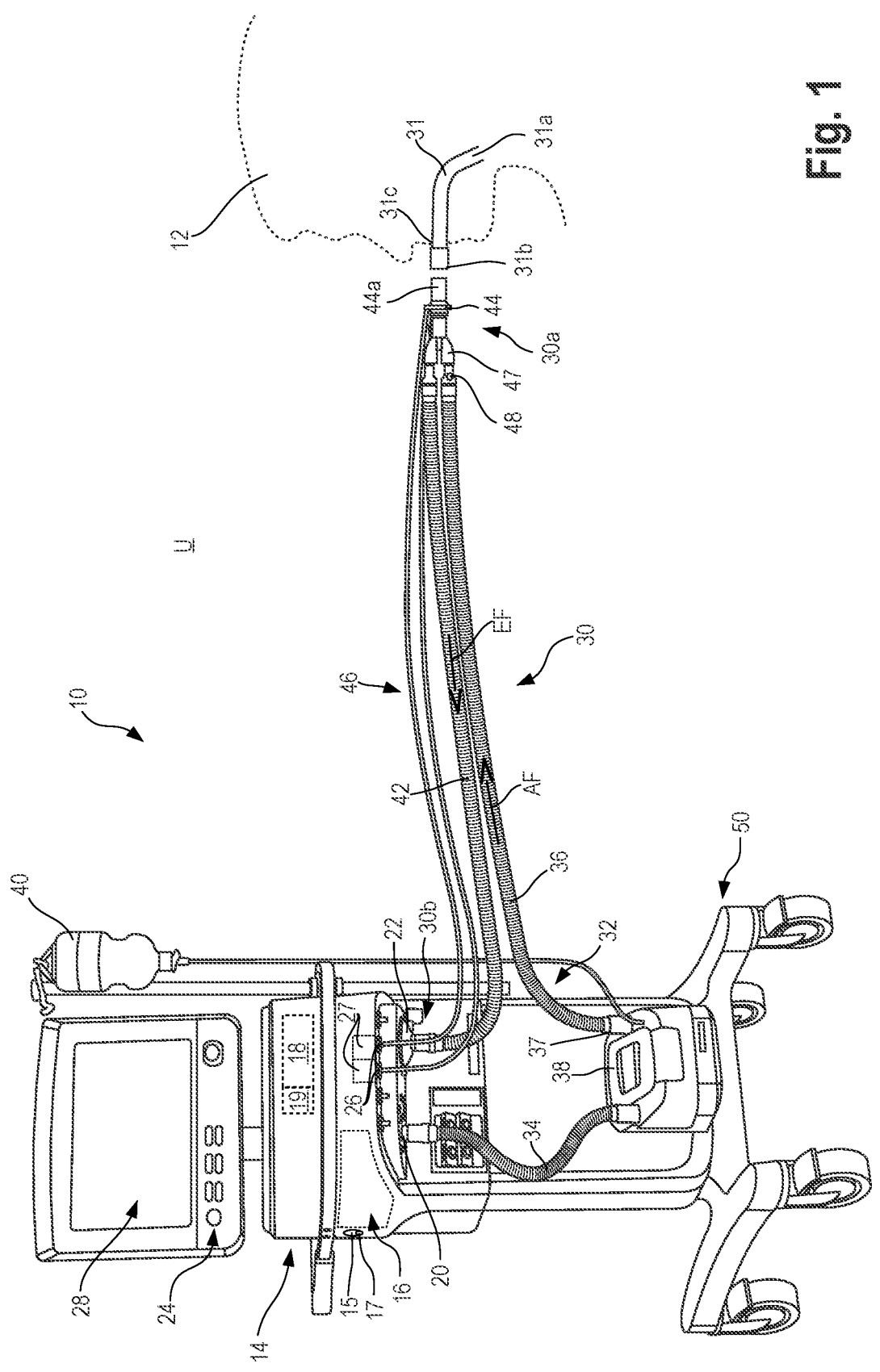
FIG. 1A schematic depiction of a ventilation device according to the invention, arranged for artificial ventilation of a patient, and FIG. 2A schematic depiction of a P-V curve obtained through a P/V maneuver of the ventilation device according to the invention and its evaluation.

Referring now to the drawings wherein the showings are for the purpose of illustrating preferred and alternative embodiments of the invention only and not for the purpose of limiting the same, in FIG. 1, an embodiment of a ventilation device according to the invention is denoted generally by 10. The ventilation device 10 serves in the depicted example for artificial ventilation of a human patient 12.

The ventilation device 10 exhibits a housing 14 in which an aspiration port 15 is configured and—not discernible from the outside because of the opaque housing material—a flow modification device 16 and a control device 18 are accommodated. The aspiration port 15 allows the flow modification device 16 to aspirate ambient air from the external environment U of the ventilation device, and after cleaning by filters in a manner known per se feed it as respiratory gas to the patient 12. The aspiration port 15 is therefore a respiratory gas source arrangement within the meaning of the present application.

In the aspiration port 15 there can be situated an ambient temperature sensor 17 which measures the temperature of the air of the environment U and transmits it to the control device 18.

The flow modification device 16 is constructed in a manner known per se and can exhibit a pump, a compressor, a fan, a pressure tank, a reducing valve, and the like. The ventilation device 10 further exhibits in a manner known per se an inspiration valve 20 and an expiration valve 22.

The control device 18 is usually realized as a computer or microprocessor. It comprises a data memory, denoted in FIG. 1 by 19, in order to be able to store and retrieve when required data needed for the operation of the ventilation device 10. In the even of network operation, the data memory 19 can also be situated outside the housing 14 and connected with the control device 18 via a data transmission link. The data transmission link can be formed by a cable or a radio path. However, in order to prevent interference in the data transmission link being able to impact the operation of the ventilation device 10, the data memory 19 is preferably integrated in the control device 18 or at least accommodated in the same housing 14 as it.

For the input of data into the ventilation device 10 and/or more precisely into the control device 18 respectively, the ventilation device 10 can exhibit an input device 24 which in the example depicted in FIG. 1 is represented by a keyboard. As is still to be explained further below, the keyboard is not necessarily the only data input of the control device 18. In fact, additionally or alternatively to the keyboard the control device 18 can receive data via various data inputs, for instance via a network cable, a radio path, or via sensor connectors 26.

In order to output data to the treating healthcare professional, the ventilation device 10 can exhibit an output device 28 exhibit, in the depicted example a monitor screen.

For artificial ventilation, the patient 12 is connected with the ventilation device 10, more precisely with the flow modification device 16 in the housing 14, via a respiratory gas line arrangement 30. To this end, the patient 12 is intubated by means of an endotracheal tube as a patient interface 31. A proximal longitudinal end 31a of the patient interface 31 delivers the inspiratory respiratory gas flow AF into the lung of the patient 12. The expiratory respiratory gas flow EF also flows through the proximal longitudinal end 31a into the respiratory gas line arrangement 30.

A distal longitudinal end 31b of the patient interface 31 is configured for connecting with the respiratory gas line arrangement 30. From the location 31c downstream in the inspiration direction up to the proximal longitudinal end 31a, the patient interface is surrounded by the body of the patient 12. Conversely, this means that from its distal longitudinal end 31b up to the location 31c, the patient interface 31 is exposed to the external environment U and is in heat transfer contact with it, predominantly convectively.

The respiratory gas line arrangement 30 exhibits an inspiration hose 32 via which fresh respiratory gas can be conducted from the flow modification device 16 into the lung of the patient 12. The inspiration hose 32 can be discontinuous and exhibit a first inspiration hose 34 and a second inspiration hose 36, between which a humidification device 38 can be provided for controlled humidification and where applicable also temperature control of the inspiratory respiratory gas supplied to the patient 12. The humidification device 38 can be connected with an external fluid reservoir 40, via which water for humidification or a medicinal product, for instance for anti-inflammatory treatment or for dilating the respiratory tract, can be delivered to the humidification device 38. When using the present ventilation device 10 as an anesthesia ventilation device, volatile anesthetics can in this way be delivered to the patient 12 in a controlled manner via the ventilation device 10. The humidification device 38 ensures that the fresh respiratory gas is supplied to the patient 12 at a predetermined humidity, where applicable with the addition of a medicinal product aerosol, and at a predetermined temperature.

In the present example, the second inspiration hose 36 is heatable electrically by a line heating device 37. The line heating device 37 can be actuated through the control device 18 for operation. The above notwithstanding, the first inspiration hose 34 can also be heatable and/or the at least one hose 34 and/or 36 can be heatable through a non-electric line heating device 37, for instance by being flushed around with a heat-exchange medium.

The respiratory gas line arrangement 30 further exhibits, besides the already mentioned inspiration valve 20 and expiration valve 22, an expiration hose 42 via which metabolized respiratory gas is discharged as an expiratory respiratory gas flow EF from the lung of the patient 12 into the external environment U.

At the distal longitudinal end 30*b* of the respiratory gas line arrangement 30, the inspiration hose 32 is coupled with the inspiration valve 20 and the expiration hose 42 with the expiration valve 22. Of the two valves, preferably only one is open at any time for the passage of a gas flow. The actuation control of the valves 20 and 22 likewise takes place through the control device 18.

During a ventilation cycle, first for the duration of the inspiration phase the expiration valve 22 is closed and the inspiration valve 20 opened, such that fresh inspiratory respiratory gas can be conducted from the housing 14 to the patient 12. A flow of the fresh respiratory gas is effected through controlled pressure elevation of the respiratory gas through the flow modification device 16. Due to the pressure elevation, the fresh respiratory gas flows into the lung of the patient 12 and expands there the body region near the lung, i.e. in particular the ribcage, against the individual elasticity of the organs near the lung. The gas pressure inside the lung of the patient 12 also increases as a result.

At the end of the inspiration phase, the inspiration valve 20 is closed and the expiration valve 22 opened. The expiration phase begins. Due to the gas pressure of the respiratory gas present in the lung of the patient 12 being elevated until the end of the inspiration phase, after the opening of the expiration valve 22 it flows into the external environment U, whereby the gas pressure in the lung of the patient 12 decreases with progressive flow duration. Once the gas pressure in the lung 12 reaches a positive end-expiratory pressure (PEEP) set at the ventilation device 10, that is, a slightly higher pressure than atmospheric pressure, the expiration phase is ended with the closing of the expiration valve 22 and is followed by a further ventilation cycle.

During the inspiration phase, the patient 12 is supplied with the ventilation tidal volume, i.e. the respiratory gas volume per breath. The ventilation tidal volume multiplied by the number of ventilation cycles per minute, that is, multiplied by the ventilation frequency, yields the minute volume of the artificial ventilation performed in the present case.

The ventilation device 10, in particular the control device 18, is preferably configured to repeatedly update and/or determine respectively during the ventilation operation ventilation operational parameters which characterize the ventilation operation of the ventilation device 10, in order to ensure that at every point in time the ventilation operation is attuned as optimally as possible to the particular patient 12 to be ventilated. Especially advantageously, the determination of one or several ventilation operational parameters takes place at the ventilation frequency, such that for each ventilation cycle ventilation operational parameters which are up-to-date and thus optimally adjusted to the patient 12 can be provided.

To this end, the ventilation device 10 can be connected for data transmission with one or several sensors which monitor the patient's condition and/or the operation of the ventilation device 10. Merely by way of an example of a series of possible sensors, FIG. 1 includes a proximal flow sensor 44 which acquires quantitatively the respiratory gas flow present in the respiratory gas line arrangement 30, namely both the inspiratory respiratory gas flow AF and then expiratory respiratory gas flow EF. The proximal flow sensor 44, preferably configured as a differential pressure sensor, can be coupled by means of a sensor line arrangement 46 with the data inputs 26 of the control device 18. The sensor line arrangement 46 can, but does not have to, comprise electrical signal transmission lines. It can likewise exhibit hoses which transmit the gas pressure present in the direction of flow on both sides of the flow sensor 44 to the data inputs 26, where they are quantified by the pressure sensors 27.

More precisely, in the preferred embodiment example the respiratory gas line arrangement 30 exhibits at its proximal longitudinal end-region 30*a* a separately configured line Y-section 47, which at its distal end-region is connected with the second inspiration hose 36 and the expiration hose 42 and which at its proximal end-region is connected with the proximal flow sensor 44.

The proximal flow sensor 44 exhibits at its proximal end-region a coupling formation 44*a* with which the patient interface 31, which instead of a tube could also be a mask, can be coupled with the proximal flow sensor 44 and consequently with the respiratory gas line arrangement 30.

The second inspiration hose 36 can exhibit at its proximal longitudinal end-region a proximal temperature sensor 48 which measures the temperature of the respiratory gas flow AF in the second inspiration hose 36 as close as possible to the patient 12 and transmits it to the control device 18.

Merely for the sake of completeness, it should be pointed out that the ventilation device 10 according to the invention can be accommodated as a mobile ventilation device 10 on a rollable rack 50.

Figure 2:
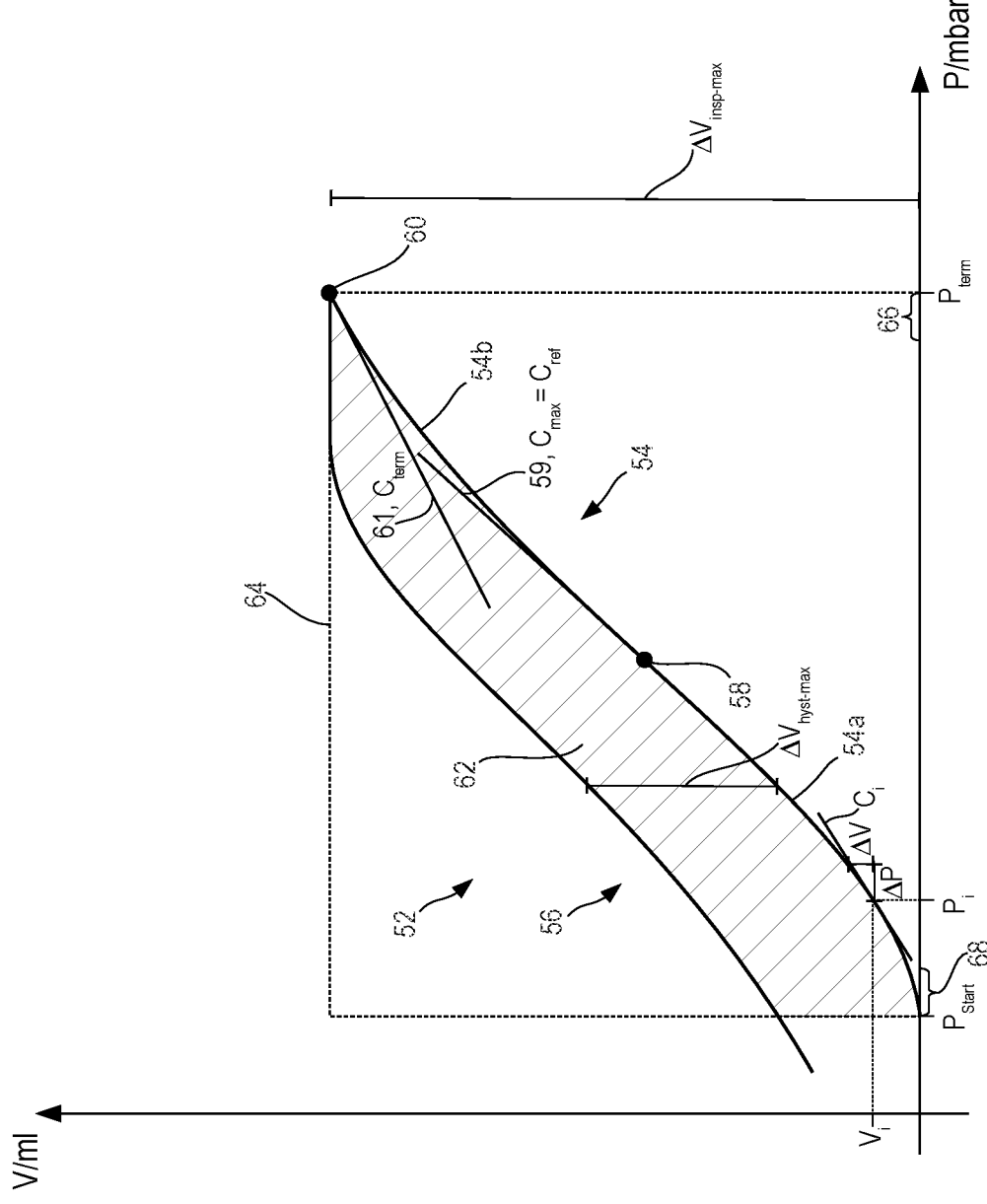

In FIG. 2, a P-V curve is depicted in rough schematic form and denoted by 52, having been obtained through a P/V maneuver performed with the ventilation device 10 of FIG. 1. The P/V maneuver of the present application can be a one-off maneuver distinct from the rest of the ventilation operation. A sequence of P/V maneuvers of the present application can, however, also be a sequence of breaths for administering the ventilation tidal volume and consequently part of the medically indicated regular artificial ventilation of the patient 12.

The abscissa of the coordinate system indicates in the direction of the arrow increasing respiratory gas pressures, the ordinate of the coordinate system indicates in the direction of the arrow increasing maneuver respiratory gas volumes. The depiction of the P-V curve in the coordinate system is merely an example and roughly schematic. The crossing point of the coordinate system is not necessarily the origin of the coordinates at a pressure of 0 mbar and a maneuver respiratory gas volume of 0 ml.

The P/V maneuver begins at a start respiratory gas pressure $P_{start}$ with an inspiration phase, i.e. the start respiratory gas pressure $P_{start}$ is sufficiently high to introduce inspiratory respiratory gas into the lung of the patient 12.

From the beginning of the inspiration phase the control device 18 acquires quantitatively, via the flow sensor 44 and the associated pressure sensors 27, the inspiratory respiratory gas flow AF and its pressure in the respiratory gas line arrangement 30, thus forming value-pairs from an inspiratory respiratory gas pressure and a maneuver respiratory gas volume associated with the pressure and administered to the patient 12. The administered maneuver respiratory gas volume corresponds to the integral of the inspiratory respiratory gas flow from the point in time of the beginning of the inspiration phase until the acquisition point in time. In tis way the control device 18 obtains the P-V curve depicted in FIG. 2. First the inspiratory branch 54 of the P-V curve 52 is obtained. After completion of the inspiration phase, the expiratory branch 56 is obtained by allowing the respiratory gas first supplied to the patient 12 escape passively, i.e. only under the pressure of the respiratory gas present in the patient 12, from the patient 12 into the environment U.

From the beginning of the inspiration phase onwards, the control device 18 determines from the difference between consecutive inspiratory respiratory gas pressures and the difference of the maneuver respiratory gas volumes associated with these respiratory gas pressures, the pulmonary compliance $C_i$ which is associated with an inspiratory respiratory gas pressure which lies quantitatively in the range—including the range boundaries 13 of inspiratory respiratory gas pressures used to determine the respiratory gas pressure difference, as a function likewise of the respiratory gas pressure. This is indicated in FIG. 2 by way of example by the gradient triangle $\Delta V/\Delta P$ at the respiratory gas pressure Pi. Referring to the P-V curve of FIG. 2, this means that the pulmonary compliance $C_i$ during the inspiration phase is the first derivative of the P-V curve with respect to the respiratory gas pressure. Consequently, in principle different methods are available and usable for determining the pulmonary compliance $C_i$ associated with a particular respiratory gas pressure.

The control device 18 stores the value-pairs thus obtained of pulmonary compliance $C_i$ and the associated respiratory gas pressure Pi in the data memory 19, and determines from the stored values the greatest occurring value $C_{max}$ of the pulmonary compliance. Here one can utilize the fact that at the beginning of each inspiration phase and at the end of each inspiration phase, lungs exhibit quantitatively lower pulmonary compliance values $C_i$ than in a middle range of the inspiration phase. If, consequently, a quantitatively greatest value $C_{max}$ of pulmonary compliances $C_i$ is reached, and if pulmonary compliances $C_i$ obtained subsequently at higher inspiratory respiratory gas pressures exhibit quantitatively lower values, then together with the quantitatively greatest value, the absolutely greatest value of the pulmonary compliance $C_{max}$ for the entire inspiration phase is also identified.

The P-V curve can be smoothed with the usual smoothing methods in order to discover noise components and thus obtain a more stable determination of the pulmonary compliance.

The greatest pulmonary compliance $C_{max}$ in FIG. 2 is at the point 58. The greatest slope present there is indicated by the tangent 59 at the inspiratory branch 54 of the P-V curve 52 at the point 58.

The value of the greatest pulmonary compliance $C_{max}$ thus determined is chosen by the control device 18 as reference compliance value $C_{ref}$. After choosing the reference compliance value $C_{ref}$, the control device 18 calculates automatically a termination compliance value $C_{term}$ at which the inspiration phase of the P/V maneuver is terminated. In the present embodiment example, the control device 18 multiplies the reference compliance value $C_{ref}$ by a predetermined factor smaller than 1, for example by 0.9, in order to calculate the termination compliance value $C_{term}$ in this way.

From now on the control device 18 compares, for increasing respiratory gas pressures, the respective determined pulmonary compliance $C_i$ with the termination compliance value $C_{term}$ and ends the inspiration phase once it has recognized that the instantaneous pulmonary compliance $C_i$ has reached or exceeded the termination compliance value $C_{term}$. This is the case in FIG. 2 at point 60, where in turn the pulmonary compliance $C_{term}$ is visualized through the tangent 61 at the inspiratory branch 54 of the P-V curve 52 at point 60.

Alternatively or additionally, the control device 18 can, from the course of the maneuver respiratory gas volumes as a function of the respiratory gas pressure, determine the point 58 as an inflection point between a concave section 54a at quantitatively lower respiratory gas pressures and a convex section 54b at quantitatively higher respiratory gas pressures as the location of the quantitatively greatest pulmonary compliance $C_{max}$ and thus as reference compliance value $C_{ref}$.

Through the termination of the inspiration phase at the point 60, the lung of the patient 12 can be protected automatically against barotrauma or other damage through pulmonary respiratory gas pressure which is too high for the particular patient 12. The termination criterion in the form of the termination compliance value $C_{term}$ is determined during the P/V maneuver to be terminated thereby and is applied right away.

In the subsequent expiration phase, represented by the branch 56 of the P-V curve 52, expiratory respiratory gas flows out of the patient's lung into the environment U in accordance with the above explanatory comments regarding FIG. 1. During this process, there sets in between the expiratory branch 56 and the inspiratory branch 54 the hysteresis which is known for P/V maneuvers.

Although pulmonary tissue can already be recruited briefly during the P/V maneuver itself, which for example can be the reason that during the expiration phase at the start respiratory gas pressure $P_{start}$, a higher maneuver respiratory gas volume is present in the patient 12 than during the inspiration phase, the hysteresis behavior of the lung of the patient 12 during the P/V maneuver is a reliable indicator for a prognosis regarding the success prospects of recruitment methods which are medically known per se on the patient's lung in order to recruit pulmonary tissue for a gas exchange.

Here the timely automated termination of the P/V maneuver before reaching excessively high inspiratory respiratory gas pressures, is also advantageous for increasing the diagnostic power of the obtained P-V curve regarding the prospects of success of a recruitment procedure in the near future for recruiting pulmonary tissue of the patient 12. Pushing the P/V maneuver ahead to predetermined high end-pressures, at which the patient's lung is already more or less strongly overdilated, would provide less diagnostically meaningful P-V curves.

For example, the control device 18 can be configured to quantify the size of the hysteresis area 62 which the two branches 54 and 56 enclose between the start respiratory gas pressure $P_{start}$ and the termination respiratory gas pressure $P_{term}$ present at the termination point 60. The control device 18 can be further configured to calculate the size of a rectangle 64 whose one corner lies at the value-pair of start respiratory gas pressure $P_{start}$ and the inspiratory maneuver respiratory gas volume associated with the start respiratory gas pressure $P_{start}$ and whose diagonally opposite corner lies at the termination respiratory gas pressure $P_{term}$ and the maneuver respiratory gas volume associated with the termination respiratory gas pressure $P_{term}$. Since at the point 60, where the termination respiratory gas pressure $P_{term}$ is present, normally the inspiratory and the expiratory maneuver respiratory gas volumes are equal, the choice of the maneuver respiratory gas volume value between the inspiratory and expiratory maneuver respiratory gas volumes is immaterial.

The control device 18 can be further configured to calculate a hysteresis ratio value from the size of the hysteresis area and the size of the rectangular area and to compare it with a predetermined first threshold value. When the hysteresis ratio value is greater than the predetermined first threshold value, the control device 18 issues via the output device 28 an output which indicates that a recruitment procedure on the currently ventilated lung has overwhelming prospects of recruiting success.

The start respiratory gas pressure $P_{start}$ can be the PEEP adjusted for the patient or up to approximately 1.6 times the adjusted PEEP. Preferably the start respiratory gas pressure of the P/V maneuver—independently of the embodiment example described here—lies in a pressure range from 5 to 8 mbar, preferably from 7 to 8 mbar.

Alternatively or additionally, the control device 18 can be configured to determine the quantitatively greatest difference between the expiratory branch 56 and the inspiratory branch 54. This is denoted by $\Delta V_{hyst\text{-}max}$ in FIG. 2.

The control device 18 can be further configured to determine the greatest volume difference of inspiratory maneuver respiratory gas volume, which usually is the difference between the volume coordinates of the inspiratory branch 54 at the termination respiratory gas pressure $P_{term}$ on the one hand and at the start respiratory gas pressure $P_{start}$ on the other. This difference is labelled $\Delta V_{insp\text{-}max}$ in FIG. 2.

The control device 18 can be further configured to calculate a volume ratio value from the greatest volume difference determined between the expiratory branch 56 and the inspiratory branch 54 and the greatest volume difference $\Delta V_{insp\text{-}max}$ of inspiratory maneuver respiratory gas volume and to compare it with a predetermined second threshold value. When the volume ratio value is greater than the predetermined second threshold value, the control device 18 again generates an output via the output device 28 according to which a recruitment procedure, performed on the currently ventilated patient's lung, has overwhelming prospects of success.

The right vertical side of the rectangle 64 in FIG. 2, and likewise the greatest inspiratory volume difference $\Delta V_{insp\text{-}max}$, lie merely especially preferably at the pressure value of the termination respiratory gas pressure $P_{term}$. The diagnostic power of the previously described criteria for assessing the prospects of a successful recruitment procedure on the patient's lung is still sufficiently reliable when the right vertical side of the rectangle 64 and/or the greatest inspiratory volume difference $\Delta V_{insp\text{-}max}$ lie in an upper end-region 66 of the respiratory gas pressure range traversed during the P/V maneuver, which extends from 95% to 100% of the termination respiratory gas pressure $P_{term}$.

Likewise, the left vertical side of the rectangle 64 can lie in a lower end-region 68 of the respiratory gas pressure range traversed during the P/V maneuver, which starting from the start respiratory gas pressure $P_{start}$ extends up to 1.05 times the start respiratory gas pressure $P_{start}$. The left vertical side of the rectangle 64 does not, therefore, have to lie directly at the start respiratory gas pressure $P_{start}$, although this is preferable.

In this way patients can, without complex computer tomography methods, be assessed directly at their ventilation site with regard to the success prospects of recruitment procedures for recruiting pulmonary tissue.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. A ventilation device for artificial ventilation of a patient, comprising:

a respiratory gas source arrangement which provides an inspiratory respiratory gas for artificial ventilation the patient, a flow modification device which is configured to produce and quantitatively modify an inspiratory respiratory gas flow, a respiratory gas line arrangement with a proximal longitudinal end which during operation lies nearer to the patient and with a distal longitudinal end which during operation lies further away from the patient, in order to convey the inspiratory respiratory gas flow from the respiratory gas source arrangement towards the patient, a flow sensor arrangement which is configured to acquire quantitatively both the inspiratory respiratory gas flow and an expiratory respiratory gas flow, a pressure sensor arrangement which is configured to acquire a pressure both of the inspiratory respiratory gas and of the expiratory respiratory gas in the respiratory gas line arrangement, a control device with a data memory, where the control device is connected for signal transmission with the data memory, with the flow sensor arrangement, and with the pressure sensor arrangement and which is configured to control the operational output of the flow modification device for modifying the inspiratory respiratory gas flow, where the control device is configured to actuate the flow modification device for performing a P/V maneuver in which in an inspiration phase, respiratory gas is supplied to a patient under elevated respiratory gas pressure which in an expiration phase after completion of the pressure elevation flows passively out of the patient, where both during the inspiration phase and during the expiration phase, for a plurality of respiratory gas pressures, the respective maneuver respiratory gas volume present in the patient due to the P/V maneuver is determined in correlation with the prevailing respiratory gas pressure, wherein the control device is configured to determine during the inspiration phase, on the basis of signals of the flow sensor arrangement and of the pressure sensor arrangement, a sequence of compliance values each of which represents a pulmonary compliance of the lung of the patient, to determine a reference compliance value in accordance with the sequence of compliance values, to determine as termination criterion for the inspiration phase, starting from the reference compliance value, a termination compliance value quantitatively different from the reference compliance value as threshold value, and to terminate the inspiration phase when the termination compliance value is reached or crossed.

2. The ventilation device according to claim 1, wherein the control device is configured to calculate the sequence of compliance values from i) a ratio of a volume change value associated with a respiratory gas pressure and a pressure change value associated with the same respiratory gas pressure, where the volume change value represents a temporal change in the maneuver respiratory gas volume and where the pressure change value represents a temporal change in the respiratory gas pressure, and/or ii) a ratio of a flow value associated with a respiratory gas pressure and the pressure change value associated with the same respiratory gas pressure, where the flow value represents the inspiratory respiratory gas flow.

3. The ventilation device according to claim 2, wherein the control device is configured to select, from a sequence of compliance values which first become quantitatively larger and subsequently smaller, the quantitatively largest compliance value as reference compliance value.

4. The ventilation device according to claim 1, wherein the control device is configured to select, from a sequence of compliance values which first become quantitatively larger and subsequently smaller, the quantitatively largest compliance value as reference compliance value.

5. The ventilation device according to claim 1, wherein the control device is configured to determine, from a sequence of value-pairs of an inspiratory respiratory gas pressure and the maneuver respiratory gas volume associated with the respective inspiratory respiratory gas pressure, an inflection point between sections curved in different directions of curvature of a graph representing the sequence of value-pairs, and to select the compliance value associated with the respiratory gas pressure at the inflection point as reference compliance value.

6. The ventilation device according to claim 1, wherein the control device is configured to calculate the termination compliance value through multiplying the reference compliance value by a predetermined factor or through adding the reference compliance value to a predetermined summand.

7. The ventilation device according to claim 6, wherein the termination compliance value equals 75% to 95% of the reference compliance values.

8. The ventilation device according to claim 7, wherein the termination compliance value equals 85% to 91% of the reference compliance values.

9. The ventilation device according to claim 1, wherein the control device is configured to calculate a volume ratio value from the quantitatively greatest difference occurring during the P/V maneuver for a respiratory gas pressure between the expiratory and the inspiratory maneuver respiratory gas volume and a difference between a maneuver respiratory gas volume value in an upper end-region and a maneuver respiratory gas volume value in a lower end-region of the respiratory gas pressure range traversed during the P/V maneuver, where the lower end-region contains a start respiratory gas pressure and extends up to 1.05 times the start respiratory gas pressure, and where the upper end-region contains a termination respiratory gas pressure with which the termination compliance value is associated and begins at 95% of the termination respiratory gas pressure.

10. The ventilation device according to claim 9, wherein the control device is configured to generate, when the volume ratio value exceeds a predetermined first threshold value, an output which indicates that a recruitment procedure for recruiting the patient's lung has overwhelming prospects of success.

11. The ventilation device according to claim 1, wherein the control device is configured to calculate a hysteresis ratio value from the size of the hysteresis area which the graphs of the expiratory and of the inspiratory maneuver respiratory gas volumes as functions of the respiratory gas pressure between a start respiratory gas pressure at which the P/V maneuver begins and a termination respiratory gas pressure with which the termination compliance value is associated, and the size of a rectangle enclosing the hysteresis area whose one corner is determined by a lower respiratory gas pressure value in a lower end-region of the respiratory gas pressure range traversed during the P/V maneuver and by the respiratory gas volume value associated with the lower respiratory gas pressure value, where the lower end-region contains the start respiratory gas pressure and extends up to 1.05 times the start respiratory gas pressure, and whose diagonally opposite corner is determined by an upper respiratory gas pressure value in an upper end-region and by the respiratory gas volume value associated with the upper respiratory gas pressure value, where the upper end-region contains a termination respiratory gas pressure with which the termination compliance value is associated and begins at 95% of the termination respiratory gas pressure.

12. The ventilation device according to claim 11, wherein the control device is configured to generate, when the hysteresis ratio value exceeds a predetermined second threshold value, an output which indicates that a recruitment procedure for recruiting the patient's lung has overwhelming prospects of success.

13. A method for performing a P/V maneuver on a patient's lung, in particular for establishing data for assessing the recruitability of pulmonary tissue, where the method comprises the following steps:

Performing a P/V maneuver and while supplying inspiratory respiratory gas to a patient in an inspiration phase under elevated respiratory gas pressure, During the inspiration phase: Determining an inspiratory maneuver respiratory gas volume supplied during the inspiration phase or an inspiratory maneuver volume flow of inspiratory respiratory gas and determining the respiratory gas pressure, Determining a sequence of compliance values each of which represents a pulmonary compliance of the lung of the patient, Determining a reference compliance value in accordance with the sequence of compliance values, Determining, starting from the reference compliance value, a termination compliance value quantitatively different from the reference compliance value as a termination threshold value, and Terminating the inspiration phase when the termination compliance value is reached or crossed.

14. The method according to claim 13, wherein an expiration phase temporally subsequent to the inspiration phase, in which respiratory gas flows passively out of the patient, where during the expiration phase both the expiratory respiratory gas pressure and an expiratory maneuver respiratory gas volume value are determined, where the expiratory maneuver respiratory gas volume value represents an expiratory maneuver respiratory gas volume present in the patient during the expiration phase due to the P/V maneuver.

15. The method according to claim 14, wherein determining the expiratory maneuver respiratory gas volume value comprises:

Determining a volume of expiratory respiratory gas exhaled during the expiration phase, and/or Determining an expiratory maneuver volume flow of expiratory respiratory gas.

16. The method according to claim 15, wherein calculation of a volume ratio value from The quantitatively greatest difference occurring during the P/V maneuver for a respiratory gas pressure between the expiratory and the inspiratory maneuver respiratory gas volume, and A difference value between a maneuver respiratory gas volume value in an upper end-region and a maneuver respiratory gas volume value in a lower end-region of the respiratory gas pressure range traversed during the P/V maneuver, Where the lower end-region contains a start respiratory gas pressure and extends up to 1.05 times the start respiratory gas pressure, and where the upper end-region contains a termination respiratory gas pressure with which the termination compliance value is associated and begins at 95% of the termination respiratory gas pressure.

17. The method according to claim 14, wherein calculation of a volume ratio value from The quantitatively greatest difference occurring during the P/V maneuver for a respiratory gas pressure between the expiratory and the inspiratory maneuver respiratory gas volume, and A difference value between a maneuver respiratory gas volume value in an upper end-region and a maneuver respiratory gas volume value in a lower end-region of the respiratory gas pressure range traversed during the P/V maneuver, Where the lower end-region contains a start respiratory gas pressure and extends up to 1.05 times the start respiratory gas pressure, and where the upper end-region contains a termination respiratory gas pressure with which the termination compliance value is associated and begins at 95% of the termination respiratory gas pressure.

18. The method according to claim 16, wherein by calculation of a hysteresis ratio value from The size of the hysteresis area which the graph of the expiratory and of the inspiratory maneuver respiratory gas volumes as functions of the respiratory gas pressure between a start respiratory gas pressure at which the P/V maneuver begins and a termination respiratory gas pressure with which the termination compliance value is associated, and The size of a rectangle enclosing the hysteresis area whose one corner is determined by a lower respiratory gas pressure value in a lower end-region of the respiratory gas pressure range traversed during the P/V maneuver and by the respiratory gas volume value associated with the lower respiratory gas pressure value, Where the lower end-region contains the start respiratory gas pressure and extends up to 1.05 times the start respiratory gas pressure and whose diagonally opposite corner is determined by an upper respiratory gas pressure value in an upper end-region and by the respiratory gas volume value associated with the upper respiratory gas pressure value, where the upper end-region contains a termination respiratory gas pressure with which the termination compliance value is associated and begins at 95% of the termination respiratory gas pressure.

19. The method according to claim 14, wherein by calculation of a hysteresis ratio value from The size of the hysteresis area which the graph of the expiratory and of the inspiratory maneuver respiratory gas volumes as functions of the respiratory gas pressure between a start respiratory gas pressure at which the P/V maneuver begins and a termination respiratory gas pressure with which the termination compliance value is associated, and The size of a rectangle enclosing the hysteresis area whose one corner is determined by a lower respiratory gas pressure value in a lower end-region of the respiratory gas pressure range traversed during the P/V maneuver and by the respiratory gas volume value associated with the lower respiratory gas pressure value, Where the lower end-region contains the start respiratory gas pressure and extends up to 1.05 times the start respiratory gas pressure and whose diagonally opposite corner is determined by an upper respiratory gas pressure value in an upper end-region and by the respiratory gas volume value associated with the upper respiratory gas pressure value, where the upper end-region contains a termination respiratory gas pressure with which the termination compliance value is associated and begins at 95% of the termination respiratory gas pressure.

* * * * *